United States Patent [19]

Okumura et al.

[11] 4,012,259

[45] Mar. 15, 1977

[54] PHOTOGRAPHIC SILVER HALIDE EMULSION AND ELEMENT AND METHOD OF FORMING COLOR PHOTOGRAPHIC IMAGES

[75] Inventors: Akio Okumura; Akira Sato; Seiji Ichijima; Keisuke Shiba; Kiyoshi Nakazyo, all of Minami-ashigara, Japan

[73] Assignee: Fuji Photo Film Co., Ltd., Minami-ashigara, Japan

[22] Filed: May 14, 1974

[21] Appl. No.: 469,923

[30] Foreign Application Priority Data

May 16, 1973 Japan .............................. 48-54456

[52] U.S. Cl. .................................. 96/56.5; 96/22; 96/74; 96/100; 260/309.2
[51] Int. Cl.² ...................... G03C 7/00; G03C 1/40
[58] Field of Search .................. 96/100, 56.2, 56.5, 96/100 N

[56] References Cited

UNITED STATES PATENTS

| | | | |
|---|---|---|---|
| 3,458,315 | 7/1969 | Loria | 96/55 |
| 3,516,831 | 6/1970 | Wolf et al. | 96/100 |
| 3,730,722 | 5/1973 | Inoue et al. | 96/56.3 |
| 3,770,436 | 11/1973 | Fujiwhara et al. | 96/56.5 |

FOREIGN PATENTS OR APPLICATIONS

| | | | |
|---|---|---|---|
| 2,213,461 | 11/1972 | Germany | 96/100 |

*Primary Examiner*—J. Travis Brown
*Attorney, Agent, or Firm*—Sughrue, Rothwell, Mion, Zinn & Macpeak

[57] ABSTRACT

A photographic silver halide emulsion containing a yellow color forming coupler, in which one hydrogen atom of an active methylene group is replaced by a 2,5-dioxo-1-imidazolidinyl group, in which a nitrogen atom at 3-position and a carbon atom at 4-position are connected to form a ring through a divalent aliphatic radical, a photographic element containing the emulsion and a method for forming color photographic images which comprises developing the image-exposed photographic silver halide emulsion with a primary aromatic amino developing agent. These yellow color forming couplers have a high coupling reactivity as well as no adverse effect on the bleaching of developed silver and thus they are suitable for use in rapid processing type color photographic materials.

35 Claims, No Drawings

PHOTOGRAPHIC SILVER HALIDE EMULSION AND ELEMENT AND METHOD OF FORMING COLOR PHOTOGRAPHIC IMAGES

BACKGROUND OF THE INVENTION

1. FIELD OF THE INVENTION

The present invention relates to a photographic silver halide emulsion, a photographic element and a method of forming color photographic images, and more particularly to color photographic materials and forming images using a yellow color forming coupler.

2. DESCRIPTION OF THE PRIOR ART

It is well known that color forming couplers couple with oxidation products of primary aromatic amino developing agents to form color photographic images. Most conventional yellow color forming couplers are four-equivalent couplers and they require four moles of exposed silver halide as oxidizing agents to form one mole of azomethine dye. An incorporation of a large amount of silver halide into light-sensitive layers leads to some disadvantages such as an increase in light scattering in the emulsion layers and consequently, a decrease in the sharpness of the images formed, and in addition, an increase in processing time of light-sensitive materials due to an increase in thickness of the emulsion layers. Furthermore, the formation of dyes with these couplers is not completed during color development and thus it is necessary to use strong oxidizing agents in subsequent processing steps.

In order to improve these defects, two-equivalent yellow color forming couplers have been provided, which require only two moles of exposed silver halide to form one mole of azomethine dye.

The two-equivalent yellow color forming couplers have, in general, chemical structures in which one of the hydrogen atoms of the active methylene group is substituted with a splittable atom or group. Examples of such splittable atoms or groups are a fluorine atom as described in U.S. Pat. No. 3,277,155, a phenoxy group as described in U.S. Pat. No. 3,408,194, an acyloxy group as described in U.S. Pat. No. 3,447,928, a sulfoxy group as described in U.S. Pat. No. 3,415,652, and a group having saccharin structure as described in German Offenlegungsschrift 2,057,941.

However, these couplers are not sufficient for use in color photography because they are accompanied by either disadvantages in that the coupling reactivity is insufficient, in that a marked color fog is produced, in that the couplers per se are unstable and their coupling activities decrease or color stain occurs in the light-sensitive materials during storage, in that the yellow color images formed are unstable or in that the preparation of the couplers is quite difficult.

As couplers which improve these defects, yellow color forming couplers having a splittable group derived from imide compounds are described in Japanese Patent Application laid open 29432/73, U.S. Patent Applications Ser. Nos. 235,937, filed Mar. 20, 1972, and 319,806, filed Dec. 29, 1972.

However, in color photographic light-sensitive materials containing the couplers described in these patent specifications, it is not easy to completely remove developed silver which is formed during a color developing step and is undesirable in the final photographs in bleach and fixing steps or in a blix step in which both bleach and fixing steps are simultaneously carried out in a mono bath. Thus it is very difficult to reduce the processing time. Also, when the developed silver is not completely removed, the color reproduction of the color images obtained is adversely affected and transparency of the images is reduced. Thus, provision of two-equivalent yellow color forming couplers which have a good silver bleaching property has been desired.

SUMMARY OF THE INVENTION

It is therefore an object of the present invention to provide a two-equivalent yellow color forming coupler having a good silver bleaching property which is suitable for use in color photographic processes based on the subtractive process for color formation.

Another object of the present invention is to provide a method of forming dye images by developing a silver halide emulsion in the presence of a novel yellow color forming coupler.

Another object of the present invention is to provide a color photographic light-sensitive material which has a silver halide emulsion layer containing a novel yellow color forming coupler.

Another object of the present invention is to provide a color developer solution containing a novel yellow color forming coupler.

Still another object of the present invention is to provide a means for reducing the amount of silver halide contained in a photographic emulsion and improving the sharpness of images formed by the use of a novel yellow color forming coupler.

Still another object of the present invention is to provide a color photographic light-sensitive material which is well suited for use in rapid color developing processing in a blix bath containing both a weak oxidizing agent and a silver complex forming agent.

A further object of the present invention is to provide yellow color images which have spectral absorption characteristics suitable for the subtractive process for color formation and good stability.

These and other objects of the present invention will appear from the following detailed description thereof.

These objects are accomplished with a photographic silver halide emulsion containing a yellow color forming coupler, in which one hydrogen atom of an active methylene group is replaced by a 2,5-dioxo-1-imidazolidinyl group, in which a nitrogen atom at the 3-position and a crabon atom at the 4-position are connected to form a ring through a divalent aliphatic group.

DETAILED DESCRIPTION OF THE INVENTION

The yellow color forming couplers which are used in the present invention can be characterized as couplers in which one of the hydrogen atoms of the active methylene group is substituted with a 2,5-dioxo-1-imidazolidinyl group and a nitrogen atom at the 3-position and a carbon atom at the 4-position of the imidazolidinyl group are bonded to each other to form a ring through a divalent aliphatic group and the imidazolidinyl group can be split off when the coupler reacts to couple with the oxidation product of a primary aromatic amino developing agent.

Of the yellow color forming couplers which can be used in the present invention, the compounds represented by the following general formula (I) are useful.

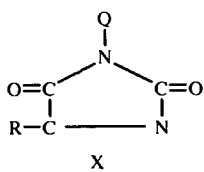

in which R represents a hydrogen atom or an alkyl group; Q represents a residue of a yellow color forming coupler having an active methylene group when one hydrogen atom attached to the active methylene group of the coupler is eliminated; and X represents a divalent aliphatic group.

As yellow color forming couplers having an active methylene group in the general formula (I), the open-chained ketomethylene yellow color forming couplers in which the active methylene group is attached directly to two carbonyl groups are suitable. Representative examples of such couplers are the α-acylacetamides. The divalent aliphatic group represented by X in the general formula (I) includes an alkylene group which can be substituted or unsubstituted and which can contain a heteroatom such as an oxygen atom, a sulfur atom or a nitrogen atom (for example, $CH_2-O-CH_2$, $CH_2-S-CH_2$, etc.).

Particularly suitable compounds of the yellow color forming couplers which can be used in the present invention are represented by the following general formula (II):

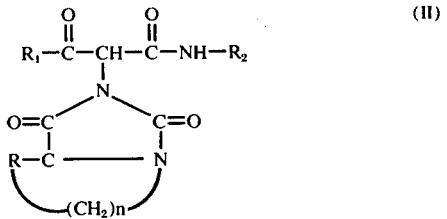

in which R represents a hydrogen atom or an alkyl group; $R_1$ represents an aliphatic group, an aromatic group or a heterocyclic group; $R_2$ represents an aromatic group or a heterocyclic group; and n represents an integer of 3 or 4.

In the general formula (II), suitable aliphatic groups represented by $R_1$ include a substituted or unsubstituted alkyl group which can be in the form of a chain or can be a cyclic group. As the substituents on the alkyl group, there can be an alkenyl group, an aryl group, an alkoxy group, an aryloxy group, an acyl group, an amino group, a carboxy group, an acylamino group, a carbamoyl group, an imido group, an alkoxy carbonyl group, an acyloxy group, a sulfo group, a sulfonyl group, a sulfonamido group, a sulfamoyl group, etc., and which in turn can be further substituted. Suitable specific examples of aliphatic groups for $R_1$ are as follows: methyl, ethyl, propyl, isopropyl, butyl, isobutyl, tert-butyl, amyl, isoamyl, tert-amyl, hexyl, 1-methylpentyl, 2-methylpentyl, neopentyl, 1,1-dimethylbutyl, heptyl, 1-methylhexyl, 2-methylhexyl, 3-methylhexyl, 5-methylhexyl, 1,1-dimethylhexyl, octyl, 2-ethylhexyl, 1,1-diethylhexyl, hexyl nonyl, isononyl, decyl, undecyl, dodecyl, tetradecyl, hexadecyl, octadecyl, 1,1-dimethylnonyldecyl, 1,1-diamylhexyl, 1-methyl-1-nonyldecyl, cyclopropyl, cyclobutyl, cyclopentyl, cyclohexyl, benzyl, phenethyl, allyl, oleyl, 7,7-dimethylnorbornyl, 1-methylcyclohexyl, 2-methoxyisopropyl, 2-benzylisopropyl, 2-phenoxyisopropyl, 2-p-tert-butylphenoxyisopropyl, 2-napthoxyisopropyl, cinnamyl, α-aminoisopropyl, α-(N,N-diethylamino) isopropyl, α-(succinimido)isopropyl, α-(phthalimido)isopropyl, α-(benzenesulfonamido)isopropyl, etc.

The aromatic groups represented by $R_1$ and $R_2$ include a substituted or unsubstituted phenyl group. Suitable substituents can be monovalent substituents such as a halogen atom, a nitro group, a thiocyano group, a hydroxy group, an alkoxy group, an aryloxy group, an acyloxy group, an alkyl group, an alkenyl group, an aryl group, an amino group, a carboxy group, an acyl group, an alkoxycarbonyl group, an aryloxycarbonyl group, a carbamoyl group, an acylamino group, an imido group, a sulfo group, an alkylsulfonyl group, an arylsulfonyl group, an alkoxysulfonyl group, an aryloxysulfonyl group, a sulfamoyl group, a sulfonamido group, an ureido group, a thioureido group, etc., and further divalent substituents which can form a condensed ring together with the phenyl group. Examples of phenyl groups having such a divalent substituent are a naphthyl group, a quinolyl group, an isoquinolyl group, a chromanyl group, a cumaranyl group, a tetrahydronaphthyl group, etc. These monovalent and divalent substituents can, in turn, have further substituents.

The heterocyclic groups represented by $R_1$ and $R_2$ are connected through a carbon atom which forms the heterocyclic ring to the carbon atom of the carbonyl group of the acyl group and the nitrogen atom of the amido group in α-acyl-acetamide, respectively. Such heterocyclic groups include those of the thiophane series (for example, 2-thienyl, 3-thienyl, 2-benzothienyl, 3-benzothienyl, 2-naphthothienyl, 3-naphthothienyl, etc.), the furan series (for example, 2-furyl, 3-furyl, 2-benzofuranyl, 3-benzofuranyl, 1-isobenzofuranyl, 3-isobenzofuranyl, etc.), the pyran series (for example, 3-pyranyl, 4-pyranyl, 5-pyranyl, 6-pyranyl, etc.), the chromene series (for example, 3-chromenyl, 4-chromenyl, etc.), the pyrrole series, the pyrazole series, the pyridine series (for example, 2-pyridyl, 3-pyridyl, 4-pyridyl, 2-quinolyl, 3-quinolyl, 4-quinolyl, 1-isoquinolyl, 3-isoquinolyl, 4-isoquinolyl, etc.), the pyrazine series (for example, 2-pyrazinyl, 2-quinoxalinyl, etc.), the pyrimidine series (for example, 2-pyrimidinyl, 4-pyrimidinyl, 5-pyrimidinyl, 2-quinazolinyl, 4-quinazolinyl, etc.), the pyridazine series (for example, 2-pyridazinyl, 3-pyridazinyl, 3-cinnolinyl, 4-cinnolinyl, etc.), the indolizinyl series (for example, 1-indolizinyl, 2-indolizinyl, 3-indolizinyl, 5-indolizinyl, 6-indolizinyl, 7-indolizinyl, etc.), the perimidine series (for example, 2-perimidinyl, etc.), the thiazole series (for example, 2-thiazolyl, 2-benzothiazolyl, 3-isothiazolyl, 4-isothiazolyl, 5-isothiazolyl, etc.), the imidazole series (for example, 2-benzoimidazole, etc.), the oxazole series, a 1,3,5-triazine series, the oxazine series, etc. These heterocyclic groups can be substituted with a halogen atom, a nitro group, a cyano group, a thiocyano group, a hydroxy group, an alkoxy group, an aryloxy group, an acyloxy group, an alkyl group an alkenyl group, an aryl group, an amino group, a carboxy group, an acyl group, an alkoxycarbonyl group, an aryloxycarbonyl group, a carbamoyl group, an acylamino group, an imido group, a sulfo group, an alkylsulfonyl group, an arylsulfonyl group, an alkoxysulfonyl group, an aryloxysulfonyl, an alkoxysulfonyl, an aryloxysulfonyl, a sulfamoyl, a sulfonamido group, an ureido group, a thioureido group, etc.

To render the yellow color forming couplers which can be used in the present invention diffusion resistant, at least one hydrophobic group having about 8 or more total carbon atoms (for example an alkylaryl group, etc.) can be introduced into the coupler molecule in a conventional manner. Various kinds of such hydrophobic groups are well known in the art, and any of them can be used in the present invention. In the 2-equivalent acylacetamide yellow color forming couplers which can be used in the present invention, such a hydrophobic group can be introduced into at least one of $R_1$ and $R_2$ in the above-described general formula (II).

It should be understood that the yellow color forming couplers represented by the general formula (II) which can be used in the present invention include compounds in which two coupler radicals are bonded each other through $R_1$ or $R_2$ as a divalent group of the monovalent groups previously described for $R_1$ or $R_2$ in the general formula (II). In such case, the yellow color forming couplers can have the following structures:

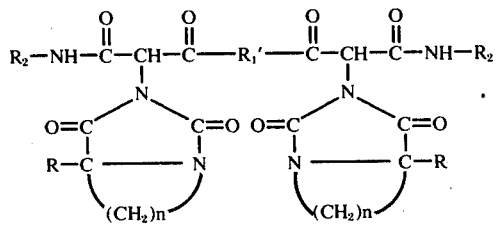

(IIa)

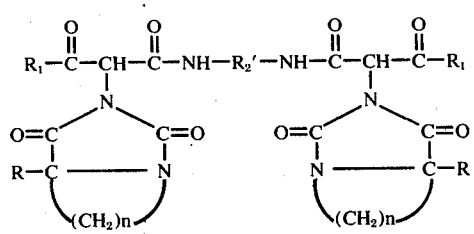

(IIb)

in which R, $R_1$, $R_2$ and n are the same as defined in the general formula (II), $R_1'$ and $R_2'$ each represents a divalent radical corresponding to $R_1$ or $R_2$ in the general formula (II).

Yellow color forming couplers in which $R_1$ in the above-described /general formula (II) is an alkyl group in which a tertiary carbon atom is bonded to the carboxyl group, particularly a tert-butyl group are preferred. Also, yellow color forming couplers in which $R_1$ is a phenyl group or phenyl group substituted with an electron-donating group such as an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an amino group (for example, amino, N,N-dimethylamino, N-butyl-N-octylamino, etc.) are preferred.

Yellow color forming couplers in which $R_2$ in the above-described general formula (II) is a phenyl group in which one of the ortho positions is substituted with a halogen atom (for example, fluorine, chlorine, bromine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino, etc.) are preferred.

Of the yellow color forming coupler which can be used in the present invention, the compounds represented by the following general formulae (III) and (IV) are particularly preferred.

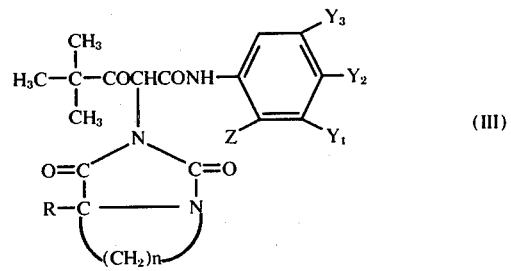

(III)

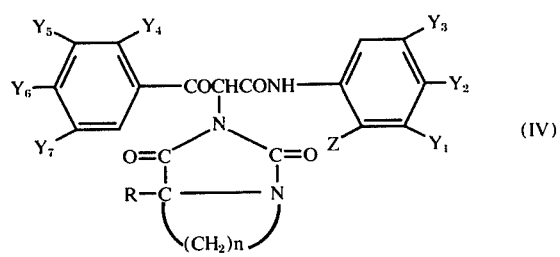

(IV)

in which R represents a hydrogen atom or an alkyl group (for example, methyl, etc.), Z represents a halogen atom (for example, fluorine, chlorine, bromine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino, etc.), $Y_1$, $Y_2$ and $Y_3$, which may be the same or different, each represents a hydrogen atom, a halogen atom (for example, fluorine, chlorine, bromine, etc.), an alkyl group (for example, methyl, ethyl, allyl, octadecyl, etc.), an alkoxy group (for example, methoxy, ethoxy, dodecyloxy, etc.), an aryl group (for example, phenyl, methylphenyl, etc.), an aryloxy group (for example, phenoxy, methylphenoxy, etc.), an alkoxy carbonyl group (for example, methoxycarbonyl, hexadecyloxycarbonyl, etc.), a carbamoyl group (for example, methylcarbamoyl, dodecylcarbamoyl, etc.), a sulfamoyl group (for example, methylsulfamoyl, diethylsulfamoyl, N-α-(2,4-di-tert-amylphenoxy)propylsulfamoyl, etc.), an alkylamino group (for example, ethylamino, N,N-dimethylamino, etc.), an arylamino group (for example, anilino, etc.), an acylamino group (for example, acetamido, α-(3-pentadecylphenoxy)butyramido, etc.), a carboxy group, a sulfo group, a cyano group or a hydroxy group, $Y_4$, $Y_5$, $Y_6$ and $Y_7$, which may be the same or different, each represents a hydrogen atom, an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc. ), an amino group (for example, an amino, N,N-dimethylamino, N-butyl-N-octylamino, etc.), or an acylamino group (for example, acetamido, α-(2,4-di-tert-amylphenoxy)butyramido, etc.), and n represents an integer of 3 or 4.

Representative examples of yellow color forming couplers which can be used in the present invention are illustrated below.

1. α-Pivaloyl-α-(2,5-dioxo-3,4-trimethylene-1-imidazolidinyl)-2'-chloro-5'-[γ-(2,4-di-tert-amylphenoxy)butyramido]acetanilide
2. α-Pivaloyl-α-(2,5-dioxo-3,4-tetramethylene-1-imidazolidinyl)-2'-chloro-5'-[γ-(2,4-di-tert-amylphenoxy)butyramido]acetanilide
3. α-Pivaloyl-α-(2,5-dioxo-3,4-trimethylene-1-imidazolidinyl)-2'-chloro-5'-[α-(2,4-di-tert-amylphenoxy)butyramido]acetanilide
4. α-Pivaloyl-α-(2,5-dioxo-3,4-tetramethylene-1-imidazolidinyl)-2'-methoxy-5'-[N-γ-(2,4-di-tert-amylphenoxy)propylsulfamoyl]acetanilide
5. α-Pivaloyl-α-(2,5-dioxo-3,4-trimethylene-4-methyl-1-imidazolidinyl)-2'-chloro-5-dodecyloxycarbonylacetanilide
6. α-Pivaloyl-α-(2,5-dioxo-3,4-tetramethylene-1-imidazolidinyl)-2'-methoxy-5'-tetradecyloxycarbonylacetanilide
7. α-(2-Methylbenzoyl)-α-(2,5-dioxo-3,4-trimethylene-1-imidazolidinyl)-2'-methoxy-5'-tetradecyloxycarbonylacetanilide
8. α-(4-Methoxybenzoyl)-α-(2,5-dioxo-3,4-trimethylene-1-imidazolidinyl)-2'-chloro-5'-[α-(2,4-di-tert-amylphenoxy)butyramido]acetanilide
9. α-(4-Methoxybenzoyl)-α-(2,5-dioxo-3,4-tetramethylene-1-imidazolidinyl)-2'-chloro-5'-[α-2,4-di-tert-amyphenoxy)butyramido]acetanilide
10. α-(2-Methylbenzoyl)-α-(2,5-dioxo-3,4-trimethylene-1-imidazolidinyl)-2-chloro-5'-hexadecyloxycarbonylacetanilide
11. α- 3-[α-(2,4-Di-tert-amylphenoxy)butyramido]-benzoyl -α-(2,5-dioxo-3,4-trimethylene-1-imidazolidinyl)-2'-methoxyacetanilide
12. α- 3-[α-(2,4-Di-tert-amylphenoxy)butyramido]-4-methoxybenzoyl -α-(2,5-dioxo-3,4-trimethylene-1-imidazolidinyl)-2'-methoxy-5'-N,N-diethylsulfamoylacetanilide
13. α-Benzoyl-α-(2,5-dioxo-3,4-tetramethylene-1-imidazolidinyl)- 2'-chloro-5'-(2-hexyldecyloxycarbonyl)acetanilide
14. α-(4-Stearoylaminobenzoyl)-α-(2,5-dioxo-3,4-trimethylene-1-imidazolidinyl)-3',5'-dicarboxyacetanilide
15. α-(4-Octadecyloxybenzoyl)-α-(2,5-dioxo-3,4-tetramethylene-1-imidazolidinyl)-2'-methoxy-5'-sulfoacetanilide
16. α-(2-Furoyl)-α-(2,5-dioxo-3,4-trimethylene-1-imidazolidinyl)-2'-chloro-5'-[α-(2,4-di-tert-amylphenoxy)butyramido]acetanilide
17. α-Pivaloyl-α-(2,5-dioxo-3,4-trimethylene-1-imidazolidinyl)-2'-chloro-4'-(N-ω-2,4-di-tert-amylphenoxybutylsulfamoyl)acetanilide
18. α-[2-Methyl-2-(4-methylphenoxy)propionyl]-α-(2,5-dioxo-3,4-trimethylene-1-imidazolidinyl)-2'-chloro-5'-[α-(3-pentadecylphenoxy)butyramido]acetanilide
19. α-(2-Ethoxy-2-methylpropionyl)-α-(2,5-dioxo-3,4-tetramethylene-1-imidazolidinyl)-2'-chloro-5'-dodecyloxycarbonylacetanilide
20. α-Benzoyl-α-(2,5-dioxo-3,4-tetramethylene-1-imidazolidinyl)-2'-methoxyacetanilide
21. α-Pivaloyl-α-(2,5-dioxo-3,4-trimethylene-1-imidazolidinyl)-2'-chloro-acetanilide
22. α-(4-Methoxybenzoyl)-α-(3,4-thiazolidinedicarboxyimido)-2'-chloro-5'-[α-(2,4-di-tert-amylphenoxy)butyramido]acetanilide
23. α-Pivaloyl-α-(3,4-thiazolidinedicarboxyimido)-2'-chloro-5'-[γ-(2,4-di-tert-amylphenoxy)-butyramido]acetanilide The two-equivalent yellow color forming couplers which can be used in the present invention can be prepared by halogenating one of the active hydrogen atoms attached to the coupling potition of 4-equivalent α-acylacetamide yellow color forming couplers with chlorine or bromine, then reacting the halogenated compound with a 2,5-dioxoimidazolidine in which the nitrogen atom at the 3-position and the carbon atom at the 4-position are connected to each other through a divalent aliphatic group to form a ring, in an organic solvent such as dimethylformamide, dimethylsulfoxide, acetonitrile, etc., in the presence of a base such as sodium hydroxide, triethylamine, etc. The 2,5-dioxoimidazolidines which can be employed as the starting material can be prepared according to the method described in *Chemical Abstracts*, 68, p. 49512, using an amino acid and potassium cyanate.

The preparation of the representative example of yellow color forming couplers is hereinafter illustrated in greater detail. Unless otherwise indicated herein, all parts, percents, ratios and the like are by weight.

SYNTHESIS EXAMPLE 1

Synthesis of α-Pivaloyl-α-(2,5-dioxo-3,4-trimethylene-1-imidazolidinyl)-2'-chloro-5'-[γ-(2,4-di-tert-amylphenoxy) butyramido]acetanilide:

To a solution containing 4g of potassium hydroxide dissolved in 15 ml of methanol, was added a solution containing 10g of 2,5-dioxo-3,4-trimethyleneimidazolidine dissolved in 50 ml of dimethylformamide, and further was added dropwise a solution containing 20g of α-pivaloyl-α-2'-chloro-5'-[γ-(2,4-di-tert-amylphenoxy) butyramido]acetanilide in 200 ml of dimethylformamide. After being stirred for 2 hours at room temperature, the reaction mixture was poured into 2l of water, and extracted with 1l of ethyl acetate. The ethyl acetate layer was separated, washed with a dilute hydrochloric acid solution, washed with water and dried over anhydrous sodium sulfate. The ethyl acetate was distilled off under reduced pressure, and the residue was recrystallized from acetonitrile, yielding 12g of the coupler. The melting point was 184°–185° C.

SYNTHESIS EXAMPLE 2

Synthesis of α-Pivaloyl-α(2,5-dioxo-3,4-tetramethylene-1-imidazolidinyl)-2'-chloro-5'-[γ-(2,4-di-tert-amylphenoxy) butyramido]acetanilide:

The reaction was carried out as described in Synthesis Example 1 except for the use of 2,5-dioxo-3,4-tetramethyleneimidazolidine in place of the 2,5-dioxo-3,4-trimethyleneimidazolidine. The product was recrystallized from a solvent mixture of ligroin and ethyl acetate to give the coupler, having a melting point of 133°–134° C.

SYNTHESIS EXAMPLE 3

Synthesis of α-(4-Methoxybenzoyl)-α-(2,5-dioxo-3,4-trimethylene-1-imidazolidinyl)-2'-chloro-5'-[α-(2,4-di-tert-amylphenoxy)butyramido]acetanilide:

The reaction was carried out as described in Synthesis Example 1 except for the use of α-(4-methoxybenzoyl)-(α-bromo-2'-chloro-5'-[α-(2,4-di-tert-amylphenoxy)butyramido]acetanilide in place of the α-pivaloyl-α-chloro-2'-chloro-5'-[γ-(2,4-di-tert-amyl-phenoxy)butyramido]acetanilide. The product was recrystallized from a solvent mixture of ethanol and hexane to give the coupler, having a melting point of 116°–118° C.

SYNTHESIS EXAMPLE 4

Synthesis of α-(4-Methoxybenzoyl)-α-(2,5-dioxo-3,4-tetramethylene-1-imidazolidinyl)-2'-chloro-5'-[α-(2,4-di-tertamylphenoxy)butyramido]acetanilide:

The reaction was carried out as described in Synthesis Example 3 except for the use of 2,5-dioxo-3,4-tetramethylene-imidazolidine in place of the 2,5-dioxo-3,4-trimethyleneimidazolidine. The product was recrystallized from a solvent mixture of ligroin and ethyl acetate to give the coupler, having a melting point of 125°–127° C.

The yellow color forming couplers according to the present invention are used by addition to photographic lightsensitive materials or color developer solutions. The diffusible couplers, such as Coupler (20), are suitably added to color developer solutions used to color develop the light-sensitive materials used for color photography which do not contain a color forming coupler. The non-diffusible couplers, such as Coupler (1) which contains a ballasting group in the molecule, are suitable for use by incorporation into photographic light-sensitive materials. Such couplers can be incorporated into photographic emulsions according to the methods using a high boiling and/or a low boiling organic solvent as described in U.S. Pat. Nos. 2,304,939; 2,322,027; 2,801,170; 2,801,171; and 2,949,360. The non-diffusible couplers, such as Coupler (14) which has a ballasting group as well as a solubilizing group such as a carboxy group or a sulfo group, are suitable for use by incorporating into photographic light-sensitive materials. Such couplers can be incorporated into a photographic emulsion in the form of an alkaline aqueous solution thereof. The terms "diffusible", "non-diffusible" and "ballasting group" have the meanings which are conventionally used in the art with respect to color forming couplers and are well understood by one of ordinary skill in the art.

In the case of dispersing the coupler of the present invention for preparing the coupler dispersion, a dispersion assistant can be advantageously used. Examples of such dispersion assistants are an anionic active agent containing a sulfonic acid, a sulfuric acid, a phosphoric acid, a carboxylic acid group, or a salt thereof; a nonionic surface active agent containing a hydroxyl group; a cationic surface active agent containing an ammonium, phosphonium, anilinium, pyridinium, etc., group; and an amphoteric surface active agent having an anionic group and a cationic group in the same molecule.

Using the yellow color forming couplers according to the present invention in the light-sensitive materials, if the amount incorporated is excessively small, a larger amount of silver halide is required to give the desired color density, and thus the thickness of the emulsion layer tends to increase, which results in not only increasing the time required for processing but in addition increasing the light scattering in the silver halide emulsion layer to reduce the sharpness of the images produced. On the other hand, if the amount of the coupler incorporated is excessively large, the couplers which are not converted into the dyes by color development remain in the emulsion layer and reduce the efficiency of coupler utilization. This is disadvantageous from an economical standpoint and results in increasing the thickness of the emulsion layer accompanied by the abovedescribed defects. Accordingly, it is preferred to use the coupler in a range of from about 0.02 to about 1.0 moles per mole of silver halide in the emulsion layer.

The yellow color forming couplers according to the present invention can be used alone or as a mixture of two or more.

According to the present invention, yellow color images can be formed during color development in the presence of the yellow color forming coupler of the present invention used in a light-sensitive material or in a color developer solution. The photographic light-sensitive materials containing the yellow color forming coupler of the present invention are subjected to an image exposure and then developed with a color developer solution containing a primary aromatic amino developing agent. Alternatively, photographic light-sensitive materials which do not contain the color image forming coupler are subjected to image exposure and then developed with a color developer solution containing the yellow color forming coupler according to the present invention together with a primary aromatic amino developing agent.

The silver halide photographic emulsions which can be used in the present invention include any known silver halide emulsion such as a silver bromide emulsion, a silver iodobromide emulsion, a silver chloroiodobromide emulsion, a silver chloride emulsion, and a silver chlorobromide emulsion or a silver halide emulsion of the so-called conversion halide type as described in, e.g., U.S. Pat. Nos. 2,592,250 and 3,622,318 and British Pat. No. 635,841.

Also, examples of the hydrophilic colloid which can be used for the coupler dispersion and the silver halide photographic emulsion are gelatin; a gelatin derivative such as acylated gelatin, graft gelatin, etc.; albumin; gum arabic; agar agar; a cellulose derivative such as acetyl cellulose, hydroxyethyl cellulose, carboxymethyl cellulose, etc.; and a synthetic resin such as polyvinyl alcohol, polyvinyl pyrrolidone, polyacrylamide, etc.

The silver halide emulsion can be chemically sensitized using active gelatin or a sulfur compound as described in U.S. Pat. Nos. 1,574,944; 1,623,499; 2,410,689; etc. Also, the emulsion can be sensitized using a salt of a noble metal such as palladium, gold, ruthenium, rhodium, platinum, etc., as described in U.S. Pat. Nos. 2,448,060; 2,399,083; 2,642,361; etc. Furthermore, the silver halide emulsion can be sensitized using a reducing agent such as a stannous salt, as described in U.S. Pat. No. 2,487,850, and also can be sensitized using a polyalkylene oxide derivative. Moreover, the silver halide emulsion can be spectrally sensitized with a cyanine dye or a merocyanine dye, as disclosed in U.S. Pat. Nos. 2,519,001; 2,666,761; 2,734,900; 2,739,964; 3,481,742; etc.

The silver halide emulsion can further contain a stabilizer such as a mercury compound, an azaindene, etc., as described in U.S. Pat. Nos. 2,886,437; 2,444,605; 2,403,927; 3,266,877; 3,397,987; etc., a plasticizer such as glycerine as described in C. E. K. Mees and T. H. James *The Theory of Photographic Process*, page 53 – 54, The Macmillan Co., New York (1966), and U.S. Pat. Nos. 2,904,434; 2,940,854; etc.

The photographic light-sensitive material of the present invention comprises a support having thereon at least one emulsion layer containing the coupler of the present invention.

As the support, examples are a cellulose ester film such as a cellulose nitrate film, a cellulose acetate film, etc.; a polyester film such as a polyethylene terephthalate film, etc., a polyvinyl chloride film, a polystyrene film, a polycarbonate film, a paper, a so-called baryta-coated paper prepared by coating barium sulfate on a paper support, a laminate film prepared by coating a cellulose ester, a polyester, a polyvinyl chloride, a polystyrene, or a polycarbonate on a paper or a baryta-coated paper, and a synthetic paper. A suitable coating amount of the silver halide can range from about $4 \times 10^{-4}$ to $4 \times 10^{-2}$, preferably $2 \times 10^{-3}$ to $2 \times 10^{-2}$, mol/m$^2$ and a suitable coating amount of the coupler can range from about $1 \times 10^{-4}$ to $1 \times 10^{-2}$, preferably $1 \times 10^{-3}$ to $5 \times 10^{-3}$, mol/m$^2$.

The photographic material of the present invention can have in addition to the above-described silver halide emulsion layers, other layers conventionally employed for constituting the color photographic material, such as, for instance, a protective layer, a filter layer, an intermediate layer, an antihalation layer, a subbing layer, a backing layer, a layer containing an ultraviolet absorber, etc. Also, as the binders for these layers, the hydrophilic colloid used for the silver halide emulsion layers can be employed.

Each layer of the color photographic material of the present invention can contain a hardening agent for the hydrophilic colloid. Typical examples of such hardening agents are aldehyde type compounds such as formaldehyde, glyoxal, succinaldehyde, glutaraldehyde, 2,3-dihydroxy-1,4-dioxane, mucochloric acid, dimethylolurea, etc.; active vinylic compounds such as divinylsulfone, methylene bismaleimide, 5-acetyl-1,3-diacryoyl-1,3,5-hexahydrotriazine, N,N',N'-triacryloyl-1,3,5-hexahydrotriazine, etc.; active halogen compounds such as 2,4-dichloro-6-oxytriazine sodium salt, 2,4-dichloro-6-methoxytriazine, sebacic acid bis-chloromethyl ester, N,N'-bis(α-chloroethylcarbamyl)-piperazine, etc.; epoxy compounds such as bis(2,3-epoxypropyl)methylpropyl ammonium para-toluene sulfonate, 1,4-bis(2',3'-epoxypropyloxy) butane, 1,3-diglycidyl-5-(γ-acetoxy-β-oxypropyl)isocyanurate, etc.; ethyleneiminic compounds such as 2,4,6-triethyleneimino-1,3,5-trazine, bis-β-ethylene-iminoethyl thioether, etc.; and methane sulfonate compounds such as 1,2-di(methanesulfonyloxy) ethane, 1,4-di(methanesulfonyloxy)butane, 1,5-di(methanesulfonyloxy)-pentane, etc., as described in U.S. Pat. Nos. 3,232,764; 3,288,775; 2,732,303; 3,635,718; 3,232,763; 2,732,316; 2,586,168; 3,103,437; 3,017,280; 2,783,611; 2,725,294; 2,725,295; 3,100,704; 2,091,537; 3,321,313; etc.

Further each layer of the photographic material can contain a coating aid such as saponin, polyethylene glycol monolauryl ether, etc., as described in U.S. Pat. Nos. 3,415,649; 3,441,413; 3,502,473; 3,514,293; 3,506,449; 3,539,352; 3,545,974; 3,507,660; 3,442,654; 3,475,174; 3,462,520; 3,493,379; 3,516,833; 3,516,835; 3,589,906; 3,617,292; 3,619,199; 3,663,229; 3,666,478; etc., an antistatic agent as described in U.S. Pat. Nos. 2,739,888; 3,428,456; 3,437,484; 3,457,076; 3,549,375; 3,549,369; 3,551,152; 3,552,972; 3,547,643; 3,546,043; 3,615,531; 3,625,695; 3,655,287; 3,653,906; 3,655,386; 3,686,368; 3,756,828; 3,754,924; etc., an ultraviolet absorber as described in U.S. Pat. Nos. 2,415,624; 3,052,636; 3,074,971; 3,085,097; 3,067,456; 3,215,536; 2,719,086; 2,537,877; 2,784,087; 2,882,150; 2,875,053; 2,739,971; 3,097,100; 3,060,029; 2,632,701; 2,858,346; 2,748,021; etc., a fluorescent whitening agent as described in U.S. Pat. Nos. 3,630,738; 3,615,544; 3,586,673; 3,434,837; British Patent Nos. 1,332,475; 1,319,763; 1,333,586; etc., an anti-irradiation dye as disclosed in U.S. Pat. No. 3,445,231, etc.

In the color photographic material containing the coupler or couplers of the present invention, any couplers other than the coupler of the present invention can also used. For instance, as a yellow dye-forming coupler there are the open chained type ketomethylenic couplers and typical examples of such couplers are benzoylacetanilide couplers, acylacetanilide couplers, etc. As a magenta dye-forming coupler, there are pyrazolone type couplers, indazolone type couplers, pyrazolobenzimidazole type couplers, cyanoacetyl type couplers, etc. Also, as cyan dye-forming couplers, there are illustrated phenol type couplers, naphthol type couplers, etc. Suitable examples of these couplers which can be used are described in U.S. Pat. Nos. 1,108,028; 2,186,849; 2,206,142; 2,343,702; 2,367,531; 2,369,489; 2,483,730; 2,436,130; 2,474,293; 2,600,788; 2,689,793; 2,728,658; 2,742,832; 2,808,329; 2,998,314; 3,046,129; 3,062,653; 3,265,506; 3,311,476; 3,408,194; 3,419,390; 3,419,391; 3,458,315; 3,476,563; 3,516,831; 3,617,291; 3,551,155; 3,511,156; 2,908,573; 3,642,485; 3,062,653; 3,558,319; etc.

Each of these couplers can have at the active carbon of the coupling position a group capable of being released on oxidative coupling with an aromatic primary amine developing agent, such as a halogen atom, an ether, thioether, acyloxy, phthalimido, hydantoin, thiocyano, sulfo, sulfino, saccharin, benzotriazole, etc., group, besides a hydrogen atom. Also, the coupler can be a so-called colored coupler having a chromophore such as a diazo group, a styryl group, etc., as a releasable group. Furthermore, the coupler can have a so-called diffusion resistant group so that the coupler is prevented from diffusing in the emulsion layers. Also, the coupler can have a group such as a sulfo group, a carboxyl group, etc., for dispersing the coupler in a micellar state as an alkali metal salt or an alkaline earth metal salt thereof.

The emulsion containing the yellow color forming coupler of the present invention can constitute at least one photographic emulsion layer of a conventional multilayer silver halide color photographic material comprising a support having thereon a blue-sensitive silver halide emulsion layer containing a yellow dye-forming coupler, a green-sensitive emulsion layer containing a magenta dye-forming coupler, and a red-sensitive emulsion layer containing a cyan dye-forming coupler. The silver halide emulsion can also be appropriately used in multilayer materials such as those disclosed in U.S. Pat. Nos. 3,582,322; 3,622,318; 3,547,640; 3,672,898; 3,516,831; 3,705,799 - 3,715,208; 3,737,312; 3,703,375; 3,379,529; 3,402,046; 3,620,747; and 3,450,536; British Patent No. 923,045; U.S. Patent Application Ser. No. 206,060, filed Dec. 8, 1971 and Ser. No. 29,666, filed Apr. 17, 1970.

The color photographic material containing the coupler of the present invention can be processed, after exposure, using known processing methods. For instance, when the photographic material of this invention is a negative-positive type negative or positive color photographic material, the color photographic material can be processed using the following main steps:

1. Color development
2. Stop or fix
3. Bleach and fix, or blix

Of these steps the second step can be omitted. Also, if desired, a hardening step for hardening the emulsion layers and an alkaline bath pre-treatment step for removing a resin backing layer can be employed before the first step, or step 1 described above. Furthermore, if desired, a hardening step can be employed between step 1 and step 2 or step 2 and step 3 or further after step 3. Still further, if desired, a stabilization step for improving the stability of images formed can be employed. Moreover, washing steps can also be employed between each step and after the last step.

After all of the photographic process steps are finished, the color photographic material is dried. That is to say, the color photographic material can be dried by natural drying by exposure to air, heating, hot-air drying, infrared radiation, electron rays, etc.

When the color photographic material containing the coupler of the present invention is used as a reversal type photographic material, the color photographic material is processed using the followng main steps:

1. Black and white development
2. Reversal exposure
3. Color development
4. Stop or fix
5. Bleach and fix or blix When the bath for color development step 3 contains a fixing agent, step 2 can be omitted. In reversal processing, a hardening step, an alkaline bath pre-treatment step, a stabilization step, and washing steps can be, if desired, employed before or after each step described above. Also, after finishing all of the processing steps, the color photograhic material is also dried as described for the aforesaid negative-positive type treatment.

For each step of the aforesaid negative-positive type treatment and the reversal type treatment, processing baths of known compositions can be used.

A useful color developer is an alkaline solution containing a color developing agent. As the color developing agent, any known aromatic primary amine developing agents can be used as disclosed, for example, in U.S. Pat. Nos. 2,592,364; 2,193,015 and C.E.K. Mees, T. H. James, *The Theory of the Photographic Process*, pages 294 – 295, Macmillan Co., (1966), such as N,N-diethyl-p-phenylene diamine, N-ethyl-N-hydroxyethyl-p-phenylene diamine, N-ethyl-N-hydroxyethyl-2-methyl-p-phenylene diamine, N-ethyl-N-β-methanesulfonamidoethyl-3-methyl-4-aminoaniline, N,N-diethyl-2-methy-p-phenylene diamine, and the sulfates, hydrochlorides, sulfites of these compounds.

The color developer used for developing the color photographic material of this invention can further contain conventional additives such as an alkali metal (e.g., sodium or potassium) sulfite, an alkali metal carbonate, an alkali metal bisulfate, an alkali metal bromide, an alkali metal iodide, benzyl alcohol, a water softener (such as sodium hexametaphosphate, an alkali metal hydroxide, hydroxylamine, a sulfate of hydroxylamine, and a hydrochloride of hydroxylamine), a competitive coupler (such as mono-sodium 1-amino-8-naphthol-3,6-disulfonate, citrazinic acid, etc.), and the like.

In addition, as described above, the color developer can contain the coupler of this invention. A suitable amount of the coupler ranges from about 0.5 to 10g, preferably 1 to 5g, per liter of the color developer.

The stop solution used in the aforesaid processings can contain a known pH-reducing agent (such as acetic acid, phthalic acid, etc.).

The fix solution can contain a known fixing agent such as sodium thiosulfate, ammonium thiosulfate, potassium thiocyanate, etc.

The bleach solution can contain a known bleaching agent such as a ferricyanide (e.g., potassium ferricyanide), a bichromate (e.g., potassium bichromate), a ferric salt of ethylenediamine tetraacetic acid, etc.

When the bleach step and the fix step are conducted in one bath, a blix bath containing a known solvent for silver halide and a known silver oxidizing agent can be used. Examples of such a silver halide solvent are a thiosulfate (e.g., ammonium or potassium thiosulfate), a thiocyanate (e.g., ammonium or potassium thiocyanate), an organic diol containing an oxygen or sulfur atom (such as 3-thio-1,5-pentanediol, 3,6-dithio-1,8-octanediol, 9-oxa-3,6,12,15-tetrathia-1,17-heptadecanediol, etc.), a sulfurcontaining organic dibasic acid or a salt thereof (such as ethylenebisthioglycolic acid, a sodium salt thereof, etc.), imidazolidinethione, and the like. Also, examples of the oxidizing agent for silver are a ferricyanide (e.g., potassium or ammonium ferricyanide), a quinone (e.g., quinone, p-benzoquinone, o-benzoquinone, p-toluquinone, 1,2-naphthoquinone), a ferric salt (e.g., a chloride or sulfate), a cupric salt (e.g., a chloride or sulfate), a cobaltic acid or salt (e.g., a chloride or sulfate), a complex salt of an ammonium ion or alkali metal ion, a ferric ion, a cupric ion, or a cobalt ion, and an organic acid (such as malonic acid, tartaric acid, ethylmalonic acid, malic acid, fumaric acid, diglycolic acid, dithioglycolic acid, ethyliminopropionic acid, nitrilotriacetic acid, ethylenediamine tetraacetic acid, aminotriacetic acid, ethylenedithioglycolic acid, dithioglycolic acid, etc.), and a chelate compound of a ferric ion, a cupric ion, or a cobalt ion (examples of coordination compounds of these chelate compounds are ethylenediamine, diethylenetriamine, triethylenetetramine, diaminopropane, diaminocyclohexane, polyethyleneimine, acetylacetone, diethyldithiocarbamate, oxyquinoline, dithizone, dipyridyl, phenanthrenine, etc., ferric ethylenediaminetetraacetic acid sodium salt, cupric malonic acid sodium salt), and the like.

These photographic processing compositions, and the components and proportions contained therein are well known in the art, as disclosed in *The Journal of the Society of Motion Picture and Television Engineers*, vol. 61, page 667 – 701; U.S. Pat. Nos. 3,189,452 and 3,582,322; L. F. A. Mason, *Photographic Processing Chemistry*, page 187 – 188, Focal Press (1966), German Pat. Nos. 886,605 and 966,410; and the *British Journal of Photography*, page 122–123, 126 (1966).

The couplers of the present invention can be used, in addition to the aforesaid color photographic materials based on the subtractive color process, for other silver halide photographic materials forming color images by color development using aromatic primary amino developing agents, such as color radiographic photographic materials, infrared photographic materials, photographic materials for radar images, color microphotographic materials, and the like.

Embodiments and features of the present invention will be further explained by reference to the followng examples.

EXAMPLE 1

A solution prepared by heating at 40° C a mixture of 54.2 g of the above-described Coupler (1), α-pivaloyl-α-(2,5-dioxo3,4-trimethylene-1-imidazolindinyl)-2′-chloro-5′-[γ-(2,4-di-tertamylphenoxy)-butyramide]acetanilide, 50 ml of di-n-butyl-phthalate and 100 ml of ethyl acetate was added to 500 ml of an aqueous solution containing 50g of gelatin and 2.5g of sodium p-dodecylbenzene sulfonate and stirred, then passed five times through a preheated colloid mill.

All of the coupler dispersion thus prepared was added to 1 kg of a photographic emulsion containing 75g of gelatin and 56.7g. of silver iodobromide (iodide content 3.0 mol%), and then 12.5 ml of a 4% aqueous solution of the sodium salt of 2-hydroxy-4,6-dichloro-s-triazine was added as a hardener. After adjusting the pH to 6.5, the mixture was coated on a cellulose triacetate film in a dry thickness of 7.0 microns to prepare a photographic light-sensitive material. This material is designated Sample A. In Sample A the coupler content coated was $2.14 \times 10^{-3}$ mol/m² and the coating amount of silver was $93.8 \times 10^{-2}$ g/m².

For comparison, a photograhic light-sensitive material was prepared by carrying out the same procedure as described for Sample A except that 51.3g of Coupler Example (15) described in Japanese Patent Application laid open 29432/73, α-pivaloyl-α-(2,5-dioxo-3-methyl-1-imidazolidinyl)-2′-chloro-5′-[γ-2,4-di-tertamylphenoxy)butyramido]acetanilide, was used in place of Coupler (1). This material is designated Sample B. In Sample B the coupler content coated was $2.16 \times 10^{-3}$ mol/m² and the coating amount of silver was $95.0 \times 10^{-2}$ g/m².

These photograhic light-sensitive materials were subjected to stepwise exposure and processed in the following manner.

| Step | Temperature | Time |
|---|---|---|
|  | (° C) | (min) |
| 1. Color Development | 20 | 15 |
| 2. Wash | 18 | 1 |
| 3. First Fixing | 20 | 4 |
| 4. Wash | 18 | 3 |
| 5. Bleach | 20 | 5 |
| 6. Wash | 18 | 3 |
| 7. Second Fixing | 20 | 3 |
| 8. Wash | 18 | 15 |

The composition of the color developer solution used was as follows:

| | |
|---|---|
| Water | 1,000 ml |
| 4-Amino-3-methyl-N,N-diethylaniline Hydrochloride | 2.5 g |
| Sodium Sulfite (anhydrous) | 3.0 g |
| Sodium Carbonate (monohydrate) | 47.0 g |
| Potassium Bromide | 2.0 g |

The fixing solution was an acidic aqueous solution containing sodium thiosulfate and sodium sulfite, and the bleach solution used was a neutral aqueous solution containing potassium ferricyanide and potassium bromide.

After processing Sample A and Sample B the transmission optical density to blue light was measured and the photographic properties obtained are shown in Table 1.

TABLE 1

| Sample | Coupler | Coating Amount of Coupler | Fog | Sensitivity* | Gamma | Max Density |
|---|---|---|---|---|---|---|
|  |  | mole/m² |  | (relative value) |  |  |
| A | (1) | $2.14 \times 10^{-3}$ | 0.22 | 100 | 2.31 | 3.17 |
| B | Comparison | $2.16 \times 10^{-3}$ | 0.23 | 99 | 2.24 | 3.13 |

*Amount of exposure required to give a density of fog + 0.10

Referring to Sample A and Sample B, the maximum densities to blue light were measured which were obtained upon treatment for different periods of color development processing time. The results shown in Table 2 were obtained.

TABLE 2

| Sample | Coupler | Developing Time (min) | | | |
|---|---|---|---|---|---|
|  |  | 5 | 10 | 15 | 20 |
| A | (1) | 2.51 | 3.16 | 3.17 | 3.15 |
| B | Comparison | 2.49 | 3.10 | 3.15 | 3.18 |

The maximum transmission densities to near infrared light of the samples obtained upon treatment for different periods of color development processing time were measured using a filter having an absorption maximum at 750 millimicrons and the results shown in Table 3 were obtained.

TABLE 3

| Sample | Coupler | Coating Amount of Coupler | Developing Time (min) | | | |
|---|---|---|---|---|---|---|
|  |  | g/m² | 5 | 10 | 15 | 20 |
| A | (1) | $93.8 \times 10^{-2}$ | 0.03 | 0.04 | 0.04 | 0.05 |
| B | Comparison | $95.0 \times 10^{-2}$ | 0.04 | 0.07 | 0.10 | 0.15 |

From these results, it can be understood that the coupler which can be used in the present invention is a superior coupler which provides a high sensitivity, latitude and color density as well as has a good silver bleaching property with less amount of developed silver remaining which is undesirable for color images in comparison with the coupler used in the comparison sample.

EXAMPLE 2

A solution prepared by heating at 40° C a mixture of 5.70g of the above-described Coupler (8), α-(4-methoxybenzoyl)-α-(2,5-dioxo-3,4-trimethylene-1-imidazolidinyl)-2′-chloro-5′-[α-(2,4-di-tert-amylphenoxy)butyramido]acetanilide, 6 ml of trin-hexyl-phosphate, 10 ml of ethyl acetate and 0.2g of the sodium salt of bis-(2-ethylhexyl)-α-sulfosuccinate was added to 100 ml of an aqueous solution containing 10g of gelatin and stirred, then agitated in a high speed agitator for 20 minutes.

All of the coupler dispersion thus prepared was added to 100g of a photographic emulsion containing 8.0 g of gelatin and $3.0 \times 10^{-2}$ mole of silver bromide, and then 6 ml of a 3% acetone solution of triethylene phosphamide was added as a hardener. After adjusting the pH to 6.5, the mixture was coated on a cellulose triacetate film in a dry thickness of 7.0 microns to prepare a photographic light-sensitive material. The material is designated Sample C. In Sample C, the coated coupler content was $2.03 \times 10^{-3}$ mole/m².

For comparison, a photographic light-sensitive material was prepared by carrying out the same procedure as for Sample C except that 5.60g of Coupler (a), α-(4-methoxybenzoyl)-α-(5',5'dimethylhydantoinyl)-2'-chloro-5'-[α-(2,4-di-tert-amylphenoxy)butyramido]acetanilide, which has the same coupler residue but a 5,5'-dimethylhydantoinyl group as a splittable group, was used. The material is designated Sample D. In Sample D, the coated coupler content was $2.04 \times 10^{-3}$ mol/m².

These samples were subjected to stepwise exposure and processed using the same process as described in Example 1 except that color development was carried out at 24° C for 12 minutes using a color developer solution of the following composition.

| Color Developer Solution | |
|---|---|
| Water | 1,000 ml |
| Benzyl Alcohol | 12.0 ml |
| Sodium Hexametaphosphate | 2.0 g |
| Sodium Sulfate (anhydrous) | 2.0 g |
| Sodium Carbonate (monohydrate) | 27.5 g |
| Hydroxylamine Sulfate | 2.5 g |
| 4-Amino-3-methyl-N-ethyl-N-(β-methanesulfonamidoethyl)aniline Sesquisulfate (monohydrate) | 4.0 g |

After processing, the transmission optical density to blue light of these samples was measured to provide the results shown in Table 4.

TABLE 4

| Sample | Coupler | Coating Amount of Coupler | Fog | Sensitivity | Gamma | Max. Density |
|---|---|---|---|---|---|---|
| | | mole/m² | | (relative value) | | |
| C | (8) | $2.03 \times 10^{-3}$ | 0.14 | 100 | 1.86 | 2.42 |
| D | (a) | $2.04 \times 10^{-3}$ | 0.14 | 99 | 1.77 | 2.38 |

The maximum densities which were obtained upon treatment for different periods of color development processing time were measured and are shown in Table 5.

TABLE 5

| Sample | Coupler | Developing Time (min) | | | |
|---|---|---|---|---|---|
| | | 4 | 8 | 12 | 16 |
| C | (8) | 1.99 | 2.42 | 2.42 | 2.41 |
| D | (a) | 1.85 | 2.35 | 2.38 | 2.36 |

From these results it can be understood that Coupler (8) used in the present invention is a superior coupler which provides a high sensitivity, latitude and maximum density in comparison with Comparison Coupler (a).

EXAMPLE 3

A solution prepared by heating at 60° C a mixture of 35.4g of the above-described Coupler (2), α-pivaloyl-α-(2,5dioxo-3,4-tetramethylene-1-imidazolidinyl)-2'-chloro-5'-[γ-(2,4di-tert-amylphenoxy)-butyramido]acetanilide, 35 ml of di-n-butyl phthalate and 70 ml of cyclohexanone was added to 1,000 ml of an aqueous solution containing 85g of gelatin and 8g of sodium dinonylnaphthalene sulfonate and stirred, then passed five times through a colloid mill preheated to 40° C.

All of the coupler dispersion thus prepared was mixed with 1 kg of a photograhic emulsion containing 37.8g of silver iodo-bromide containing 2 mol% of iodide and 75g of gelatin, and then 50 ml of a 3% acetone solution of triethylene phosphamide was added as a hardener. After adjusting the pH to 6.5, the mixture was coated on a paper which had been resin-coated with polyethylene on both surfaces, in a dry thickness of 4.0 microns. On the coating a gelatin solution was coated in a dry thickness of 1.0 micron as a second layer. A green-sensitive silver halide emulsion containing a magenta color forming Coupler (b) of the structure shown below was then coated in a dry thickness of 3.5 microns as a third layer.

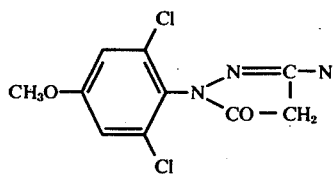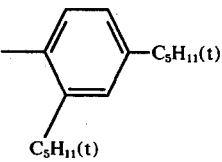

Coupler (b)

A gelatin solution containing 2-(2'-benzotriazolyl)-4,6-dibutyl-phenol as an ultraviolet absorbing agent was coated in a dry thickness of 2.5 microns as a fourth layer.

A red-sensitive silver halide emulsion containing a cyan color forming Coupler (c) of the structure shown below was coated in a dry thickness of 4.0 microns as a fifth layer.

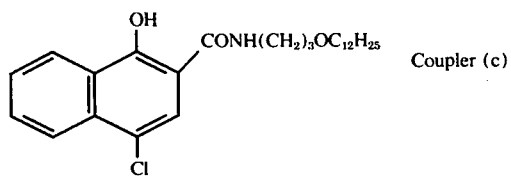

Coupler (c)

Further, a gelatin solution was coated in a dry thickness of 0.5 microns as an uppermost layer, thereby producing a color printing paper.

The color printing paper was image-exposed through a color negative as an original and processed in the following manner.

| Step | Temperature (° C) | Time (min) |
| --- | --- | --- |
| 1. Color Development | 24 | 6 |
| 2. Stop | 24 | 2 |
| 3. Blix | 24 | 6 |
| 4. Wash | 24 | 5 |

The color developer solution used was the same solution as used in Example 2, and the compositions of other processing solutions were as follows:

| Stop Solution | |
| --- | --- |
| Water | 1,000 ml |
| Sodium Sulfite (anhydrous) | 5.0 g |
| Glacial Acetic Acid | 15.0 ml |
| Blix Solution | |
| Water | 1,000 ml |
| Ammonium Thiosulfate | 105.0 g |
| Sodium Sulfite | 8.0 g |
| Sodium Hydroxide | 18.0 g |
| EDTA (disodium salt) | 35.0 g |
| Ferric Chloride (hexahydrate) | 25.0 g |
| Potassium Thiocyanate | 10.0 g |

The color print thus obtained had a clear color and exhibited excellent color reproducibility. Particularly, the yellow color which was free from a reddish tint and had a good clearness and brightness was formed. The yellow dye image had an absorption maximum at 444 millimicrons.

The color print was directly exposed to sun light for 10 days, and the density decreases for the yellow dye image were 0.06, 0.05 and 0.04 in the area of an initial reflection density of 0.5, 1.0 and 1.5, respectively.

EXAMPLE 4

A solution prepared by heating on a steam bath at 40° C a mixture of 29.8g of the above-described Coupler (9), α-(4-methoxybenzoyl)-α-(2,5-dioxo-3,4-tetramethylene-1-imidazolidinyl)2'-chloro-5'-[α-(2,4-di-tert-amylphenoxy)butyramido]acetanilide, 30 ml of tris(2-ethylhexyl)phosphate, 1.0g of 2-tert-octylhydroquinone and 60 ml of ethyl acetate was added to 300 ml of an aqueous solution containing 1.5g of sodium p-dodecylbenzene sulfonate and 30g of gelatin and stirred, then passed five times through a preheated colloid mill.

All of the coupler dispersion thus prepared was added to 700 g of a photographic emulsion containing 33.5g of silver iodobromide containing 3.0 mole% of iodide and 52.5g of gelatin, and then 8.5 ml of a 4% aqueous solution of the sodium salt of 2-hydroxy-4,6-dichloro-s-triazine was added as a hardener. After adjusting the pH at 6.0, a coating solution for a blue-sensitive emulsion layer was prepared.

On a polyethylene terephthalate film base, there were coated, as a first layer, a gelatin solution containing black colloidal silver in a dry thickness of 2.5 microns for antihalation; as a second layer, a red-sensitive silver halide emulsion containing a cyan color forming Coupler (d), 4,6-dichloro5-methyl-2-[α-2,4-di-tert-amylphenoxy)acetamido]phenol in a dry thickness of 4.5 microns; as a third layer, a gelatin solution containing 2,5-di-tert-octylhydroquinone in a dry thickness of 1.5 microns; as a fourth layer, a green-sensitive silver halide emulsion layer containing the above-described magenta color forming Coupler (b) in a dry thickness of 4.5 microns; and as a fifth layer, a gelatin layer containing yellow colloidal silver in a dry thickness of 2.0 microns. On the fifth layer, there were coated the above-described coating solution for the blue-sensitive emulsion layer in a dry thickness of 5.0 microns, and as an uppermost layer, a gelatin protective layer in a dry thickness of 1.0 micron, thereby preparing a color photographic film.

The film was exposed to light and subjected to the following processing.

| Step | Temperature (° C) | Time (min) |
| --- | --- | --- |
| First Development (black and white) | 21 | 5 |
| Wash | 18 | 10 |
| Reversal Exposure | | |
| Second Development (color) | 21 | 12 |
| Stop | 21 | 2 |
| Blix | 18 | 10 |
| Wash | 18 | 10 |

In the second development the color developer solution used in Example 2 was used, and in the blix the blix solution used in Example 3 was used. In the first development a black and white developer of the following composition was used.

| Developer Solution | |
| --- | --- |
| Water | 1,000 ml |
| p-N-Methylaminophenol | 0.3 g |
| Sodium Sulfite (anhydrous) | 38.0 g |
| Sodium Carbonate (monohydrate) | 22.5 g |
| Potassium Bromide | 0.9 g |
| Citric Acid | 0.7 g |
| Potassium Thiocyanate | 1.0 g |

The reversal color image thus obtained had a clear color and exhibited excellent color reproductibility, as well as a superior clearness due to good silver bleaching property.

While the invention has been described in detail and with reference to specific embodiments thereof, it will be apparent to one skilled in the art that various changes and modifications can be made therein without departing from the spirit and scope thereof.

What is claimed is:

1. A method of forming color photographic images which comprises developing an image-exposed photographic silver halide emulsion layer with a primary aromatic amino developing agent in the presence of a yellow color forming coupler, said coupler having an open chain active methylene group bonded to two adjacent carbonyl groups, one of the hydrogen atoms of the active methylene group being substituted by a 2,5-dioxo-1-imidazolidinyl group, in which the nitrogen atom at the 3-position and the carbon atom at the 4-position are connected to form a ring through a divalent aliphatic group having 3 or 4 carbon atoms.

2. The method of forming color photographic images as claimed in claim 1, wherein said yellow color forming coupler has the general formula (I):

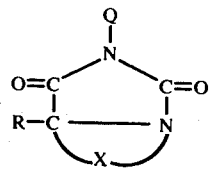

(I)

in which R represents a hydrogen atom or an alkyl group; Q represents an open chain active methylene group bonded to two adjacent carbonyl groups, one hydrogen atom of the open methylene group being eliminated; and X represents an alkylene group having 3 or 4 carbon atoms.

3. The method of forming color photographic images as claimed in claim 2, in which the open-chain methylene group represented by Q is a residue of an open-chained ketomethylene yellow color forming coupler.

4. The method of forming color photographic images as claimed in claim 2, in which said residue represented by Q is a residue of an α-acylacetamide.

5. The method of forming color photographic images as claimed in claim 2, wherein said yellow color forming coupler has the general formula (II):

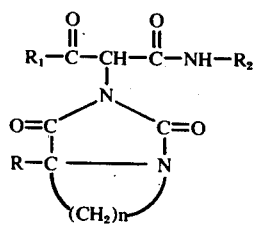

(II)

in which R represents a hydrogen atom or an alkyl group; $R_1$ represents an aliphatic group, an aromatic group or a heterocyclic group; $R_2$ represents an aromatic group or a heterocyclic group; and $n$ represents 3 or 4, wherein $R_1$, when it is said heterocyclic group, is bonded to the carbon atom of the shown carbonyl group of the acyl of said coupler through a carbon atom which forms a part of said heterocyclic group, and wherein $R_2$, when it is said heterocyclic group, is bonded to the nitrogen atom of the shown amide group of said coupler through a carbon atom which forms a part of said heterocyclic group.

6. The method of forming color photographic images as claimed in claim 5, in which said aliphatic group represented by $R_1$ is a tert-butyl group.

7. The method of forming color photographic images as claimed in claim 5, in which said aromatic group represented by $R_1$ is a phenyl group or a phenyl group substituted with an electron-donating group selected from the class consisting of an alkyl group, an alkoxy group, an aryloxy group, or an amino group.

8. The method of forming color photographic images as claimed in claim 5, in which said aromatic group represented by $R_2$ is a phenyl group in which one of the ortho positions is substituted by a halogen atom, an alkyl group, an alkoxy group or an N-substituted amino group.

9. The method of forming color photographic images as claimed in claim 2, wherein said yellow color forming coupler has the general formula (III):

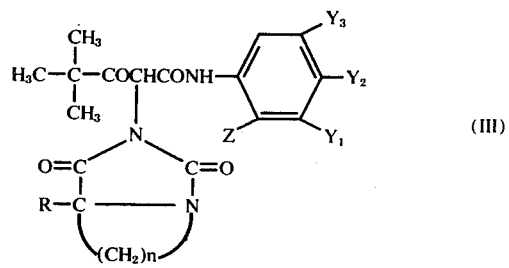

(III)

in which R represents a hydrogen atom or an alkyl group; Z represents a halogen atom, an alkyl group, an alkoxy group; and aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; and $n$ represents 3 or 4.

10. The method of forming color photographic images as claimed in claim 2, wherein said yellow color forming coupler has the general formula (IV)

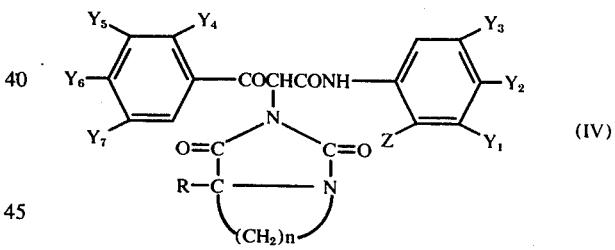

(IV)

in which R represents a hydrogen atom or alkyl group; Z represents a halogen atom, an alkyl group, an alkoxy group, an aryloxy group or a substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group, or a hydroxy group; $Y_4$, $Y_5$, $Y_6$ and $Y_7$ each represents a hydrogen atom, an alkyl group, an alkoxy group, an aryloxy group, an amino group or an acylamino group; and $n$ represents 3 or 4.

11. A photographic silver halide emulsion containing a yellow color forming coupler, said coupler having an open chain active methylene group bonded to two adjacent carbonyl groups, one of the hydrogen atoms in the methylene group being substituted by a 2,5-dioxo-1-imidazolidinyl group, in which the nitrogen atom at the 3-position and the carbon atom at the 4-position are connected to form a ring through an alkylene group having 3 or 4 carbon atoms.

12. The photographic silver halide emulsion as claimed in claim 11, wherein said yellow color forming coupler has the general formula (I):

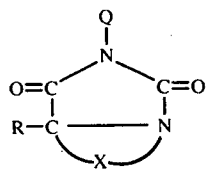

(I)

in which R represents a hydrogen atom or an alkyl group; Q represents an open chain methylene group bonded to two adjacent carbonyl groups, one of the hydrogen atoms in the methylene group is eliminated; and X represents an alkylene group having 3 or 4 carbon atoms.

13. The photographic silver halide emulsion as claimed in claim 11, wherein said yellow color forming coupler has the general formula (II)

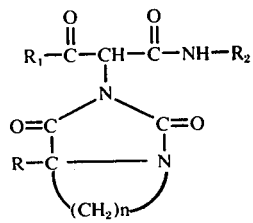

(II)

in which R represents a hydrogen atom or an alkyl group; $R_1$ represents an aliphatic group, an aromatic group or a heterocyclic group; $R_2$ represents an aromatic group or a heterocyclic group; and $n$ represents 3 or 4, wherein $R_1$, when it is said heterocyclic group, is bonded to the carbon atom of the shown carbonyl group of the acyl of said coupler through a carbon atom which forms a part of said heterocyclic group, and wherein $R_2$, when it is said heterocyclic group, is bonded to the nitrogen atom of the shown amide group of said coupler through a carbon atom which forms a part of said heterocyclic group.

14. The photographic silver halide emulsion as claimed in claim 13, in which said aliphatic group represented by $R_1$ is a tert-butyl group.

15. The photographic silver halide emulsion as claimed in claim 13, in which said aromatic group represented by $R_1$ is a phenyl group or a phenyl group substituted with an electron-donating group selected from the class consisting of an alkyl group, an alkoxy group, or an amino group.

16. The photographic silver halide emulsion as claimed in claim 13, in which said aromatic group represented by $R_2$ is a phenyl group in which one of the ortho positions is substituted by a halogen atom, an alkyl group, an alkoxy group or an N-substituted amino group.

17. The photographic silver halide emulsion as claimed in claim 11, wherein said yellow color forming coupler has the general formula (III):

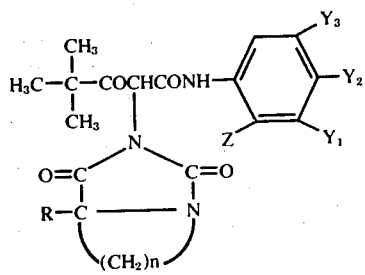

(III)

in which R represents a hydrogen atom or an alkyl group; Z represents a halogen atom, an alkyl group, an alkoxy group; an aryloxy group, or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; and $n$ represents 3 or 4.

18. The photographic silver halide emulsion as claimed in claim 11, wherein said yellow color forming coupler has the general formula (IV):

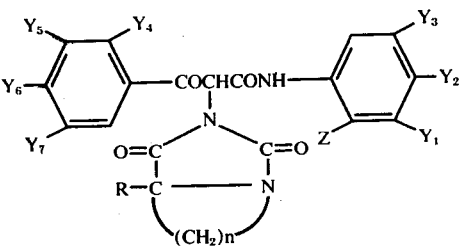

(IV)

in which R represents a hydrogen atom or an alkyl group; Z represents a halogen atom, an alkyl group, an alkoxy group, an aryloxy group or a substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group, or a hydroxy group; $Y_4$, $Y_5$, $Y_6$ and $Y_7$ each represents a hydrogen atom, an alkyl group, an alkoxy group, an aryloxy group, an amino group or an acylamino group; and $n$ represents 3 or 4.

19. The photographic silver halide emulsion as claimed in claim 11, wherein said yellow color forming coupler is α-pivaloyl-α-(2,5-dioxo-3,4-trimethylene-1-imidazolidinyl)-2'-chloro-5'-[γ-(2,4-di-tert-amyl-phenoxy)butyramido]acetanilide.

20. The photographic silver halide emulsion as claimed in claim 11, wherein said yellow color forming coupler is α-pivaloyl-α-(2,5-dioxo-3,4-trimethylene-1-imidazolidinyl)-2'-chloro-5'-[α-(2,4-di-tert-amyl-phenoxy)butyramido]acetanilide.

21. The photographic silver halide emulsion as claimed in claim 11, wherein said yellow color forming coupler is α-(4-methoxybenzoyl)-α-(2,5-dioxo-3,4-trimethylene-1-imidazolidinyl)-2'-chloro-5'-[α-(2,4-di-tert-amylphenoxy)butyramido]acetanilide.

22. The photographic silver halide emulsion as claimed in claim 11, wherein said yellow color forming coupler is α-(2-methylbenzoyl)-α-(2,5-dioxo-3,4-trimethylene-1-imidazolidinyl)-2'-chloro-5'-hexadecyloxycarbonylacetanilide.

23. A photographic light-sensitive material which comprises a support having thereon the silver halide emulsion as claimed in claim 12.

24. The photographic light-sensitive material as claimed in claim 23, wherein said yellow color forming coupler has the general formula (I):

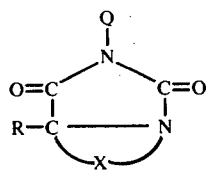

(I)

in which R represents a hydrogen atom or an alkyl group; Q represents an open chain methylene group bonded to two adjacent carbonyl groups in which one hydrogen atom attached to an active methylene group is eliminated; and X represents an alkylene group having 3 or 4 carbon atoms.

25. The photographic light-sensitive material as claimed in claim 23, wherein said yellow color forming coupler has the general formula (II):

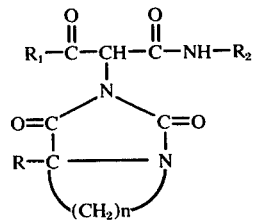

(II)

in which R represents a hydrogen atom or an alkyl group; $R_1$ represents an aliphatic group, an aromatic group or a heterocyclic group; $R_2$ represents an aromatic group or a heterocyclic group; and n represents 3 or 4, wherein $R_1$, when it is said heterocyclic group, is bonded to the carbon atom of the shown carbonyl group of the acyl of said coupler through a carbon atom which forms a part of said heterocyclic group, and wherein $R_2$, when it is said heterocyclic group, is bonded to the nitrogen atom of the shown amide group of said coupler through a carbon atom which forms a part of said heterocyclic group.

26. The photographic light-sensitive material as claimed in claim 23, wherein said yellow color forming coupler has the general formula (III):

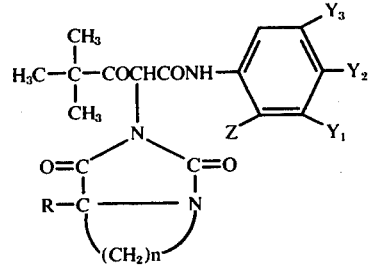

(III)

in which R represents a hydrogen atom or an alkyl group; Z represents a halogen atom, an alkyl group, an alkoxy group; an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; and n represents 3 or 4.

27. The photographic light-sensitive material as claimed in claim 23, wherein said yellow color forming coupler has the general formula (IV):

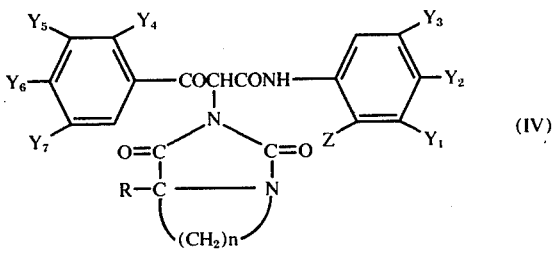

(IV)

in which R represents a hydrogen atom or an alkyl group; Z represents a halogen atom, an alkyl group, a alkoxy group, an aryloxy group or a substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group, or a hydroxy group; $Y_4$, $Y_5$, $Y_6$ and $Y_7$ each represents a hydrogen atom, an alkyl group, an alkoxy group, an aryloxy group, an amino group or an acylamino group; and n represents 3 or 4.

28. The method of forming color photographic images as claimed in claim 5, wherein said heterocyclic group is selected from the class consisting of a heterocyclic group of the thiophane series, the furan series, the pyran series, the chromene series, the pyrrole series, the pyrazole series, the pyridine series, the pyrazine series, the pyrimidine series, the pyridazine series, the indolizinyl series, the thiazole series, the imidazole series, the oxazole series, a 1,3,5-triazine series, and the oxazine series.

29. The photographic silver halide emulsion as claimed in claim 13, wherein said heterocyclic group is selected from heterocyclic groups of the thiophane series, the furan series, the pyran series, the chromene series, the pyrrole series, the pyrazole series, the pyridine series, the pyrazine series, the pyrimidine series, the pyridazine series, the indolizinyl series, the thiazole series, the imidazole series, the oxazole series, a 1,3,5-triazine series, and the oxazine series.

30. The photographic light-sensitive material as claimed in claim 25, wherein said heterocyclic group is selected from heterocyclic groups of the thiophane series, the furan series, the pyran series, the chromene series, the pyrrole series, the pyrazole series, the pyridine series, the pyrazine series, the pyrimidine series, the pyridazine series, the indolizinyl series, the thiazole series, the imidazole series, the oxazole series, a 1,3,5-triazine series, and the oxazine series.

31. The photographic silver halide emulsion as claimed in claim 12, in which said residue represented by Q is a residue of an α-acylacetamide.

32. The photographic light-sensitive material as claimed in claim 24, in which said residue represented by Q is a residue of an α-acylacetamide.

33. The method of claim 4, wherein said alkylene group is represented by the formula $(CH_2)_n$ wherein $n$ represents 3 or 4.

34. The photographic silver halide emulsion as claimed in claim 31, wherein said alkylene group is represented by the formula $(CH_2)_n$ wherein $n$ represents 3 or 4.

35. The photographic silver halide emulsion as claimed in claim 32, wherein said alkylene group is represented by the formula $(CH_2)_n$ wherein $n$ represents 3 or 4.

* * * * *